United States Patent [19]

Zobel

[11] 4,278,094
[45] Jul. 14, 1981

[54] PACEMAKER WITH PULSE WIDTH ADJUSTMENT CIRCUITRY

[75] Inventor: Don W. Zobel, Mesa, Ariz.

[73] Assignee: Medtronic, Inc., Minneapolis, Minn.

[21] Appl. No.: 83,374

[22] Filed: Oct. 10, 1979

[51] Int. Cl.³ ............................................. A61N 1/36
[52] U.S. Cl. ............................................. 128/419 PG
[58] Field of Search ................................. 128/419 PG

[56] References Cited

U.S. PATENT DOCUMENTS

| 3,746,005 | 7/1973 | Thaler et al. | 128/419 PG |
| 3,842,844 | 10/1974 | Alferness | 128/419 PG |
| 4,164,945 | 8/1979 | Hartlaub | 128/419 PG |

Primary Examiner—William E. Kamm
Attorney, Agent, or Firm—Schroeder, Siegfried, Ryan, Vidas, Steffey & Arrett

[57] ABSTRACT

A cardiac pacemaker pulse generator utilizing digital circuitry for controlling the provision of cardiac stimulating pulses. The width of the pulses is increased as the battery voltage decreases to maintain the energy of the stimulation pulse. The pulse width of each pacemaker pulse is determined by comparing a reference signal to an incrementally increasing signal which is related to the battery voltage.

6 Claims, 3 Drawing Figures

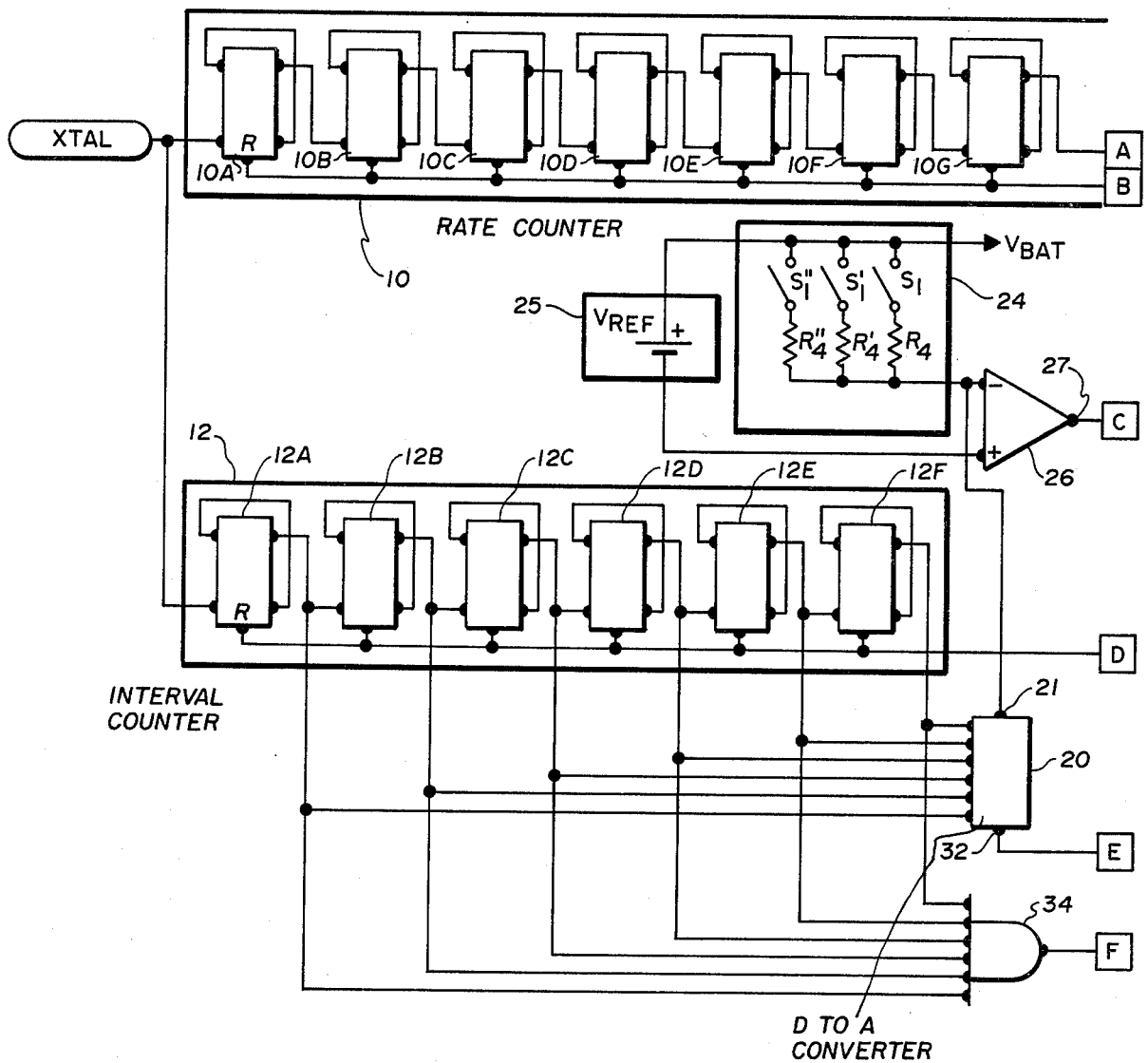

PACEMAKER WITH PULSE WIDTH ADJUSTMENT CIRCUITRY

DESCRIPTION

Background of Prior Art

This invention relates to body tissue stimulators and more particularly to an implantable cardiac pacemaker. Cardiac pacemakers were first disclosed by Greatbatch, in U.S. Pat. No. 3,057,356, entitled "Medical Cardiac Pacemaker", which issued in 1962. The device disclosed by Greatbatch included a relatively simple relaxation oscillator that generated electrical pulses at a fixed rate. These pulses were applied to the heart through a lead consisting of a conductor wire and an electrode to cause the heart to contract each time a pulse occurred.

Since 1962, many improvements to cardiac pacemakers have occurred. These improvements include increased sophistication to the circuitry, including inclusion of circuitry to alter the pulse width or energy to provide adequate stimulation without undue battery drain. Control of the amplitude or duration of the pacing pulse is desirable to permit stimulation at levels just above the threshold requirements of the particular patient, since use of higher energy pulses reduces total battery life and may produce undesired physiological results.

U.S. Pat. No. 3,198,195, to Chardack, entitled "Implantable Controls for Cardiac Pacemakers", pertains to a cardiac pacemaker including amplitude controls which are implantable with the pacemaker and require actuation by manipulation of controls from outside the body. To gain access to the controls requires a percutaneous puncture and insertion of an adjustment tool.

U.S. Pat. No. 3,833,005, to Wingrove, entitled "Compared Count Digitally Controlled Pacemaker", also pertains to a cardiac pacer having adjustable rate and/or pulse width controls. The device in that patent utilizes externally generated coded set signals to control the adjustable rate and/or pulse width of the pacing pulse.

U.S. Pat. No. 3,901,247, to Walmsley, entitled "End Of Life Increased Pulse Width and Rate Change Apparatus", discloses pulse generating circuitry used in an adjustable pulse width pacemaker. The circuitry increases the output pulse width as the power source output is decreased below a predetermined level. The circuit makes no alteration of the pulse width until the voltage level drops below the threshold value, at which time a fixed and predetermined increase in the pulse width occurs in one step. At the same time that the pulse width is increased, the output pulse rate is decreased to provide an externally detectable indication that the voltage level had decreased below the threshold value. An externally actuated potentiometer is used to predetermine the amount by which a pulse is increased when the supply voltage drops below the threshold value. The circuit does not provide for continuous variation in the width of the pacing pulse as the supply voltage decreases.

U.S. Pat. No. 3,842,844, to Alferness, entitled "Electro Medical Pulse Generator With Continuous Pulse Width Adjustment Circuitry", relates to a pulse generator for providing continuous pulse width adjustment utilizing a timing circuit incorporating a capacitor for determination of pulse width in response to decreases in reference voltage. The circuit responds to each decrease in reference voltage in a manner to keep the energy of the pulses from the pulse generator above a predetermined energy level over a wide range of voltage decreases.

United States Patent Application Ser. No. 957,958, to McDonald, entitled "Digital Cardiac Pacemaker", utilizes digital circuit techniques to automatically increase the width, or time duration, of the cardiac stimulating pulses as the voltage of the power source decreases. The digital circuit disclosed utilizes a voltage controlled oscillator to provide a chain of pulses having a frequency related to the voltage provided by the battery means, and utilizes counter means for counting voltage controlled oscillator pulses. The counter is reset to an initial count in response to the rate signal. An output circuit is also provided which is responsive to the counter to provide a cardiac stimulating pulse at a voltage related to the battery voltage from the time the counter is reset by the rate signal until the counter means reaches a predetermined value.

BRIEF SUMMARY OF THE INVENTION

In accordance with one aspect of this invention, there is provided a circuit for stretching the pulse width of a pacing pulse to achieve constant output pulse energy as the power source decreases in voltage. The system eliminates the need to use a voltage controlled oscillator which would inherently require use of a capacitor and cause the circuit to be inefficient from a current drain standpoint. The pulse width stretching circuitry of the present invention utilizes a unique digital to analog converter not requiring use of a capacitor or a voltage controlled oscillator. The circuit disclosed herein also eliminates the drift and trim problems which would arise through the use of a voltage controlled oscillator capacitor.

BRIEF DESCRIPTION OF THE DRAWINGS

There is hereafter described a preferred embodiment of the subject invention with reference being made to the following figures in which:

FIGS. 1A and 1B are schematics of a cardiac pacing circuit according to the present invention.

DETAILED DESCRIPTION OF INVENTION

Figure 1B:
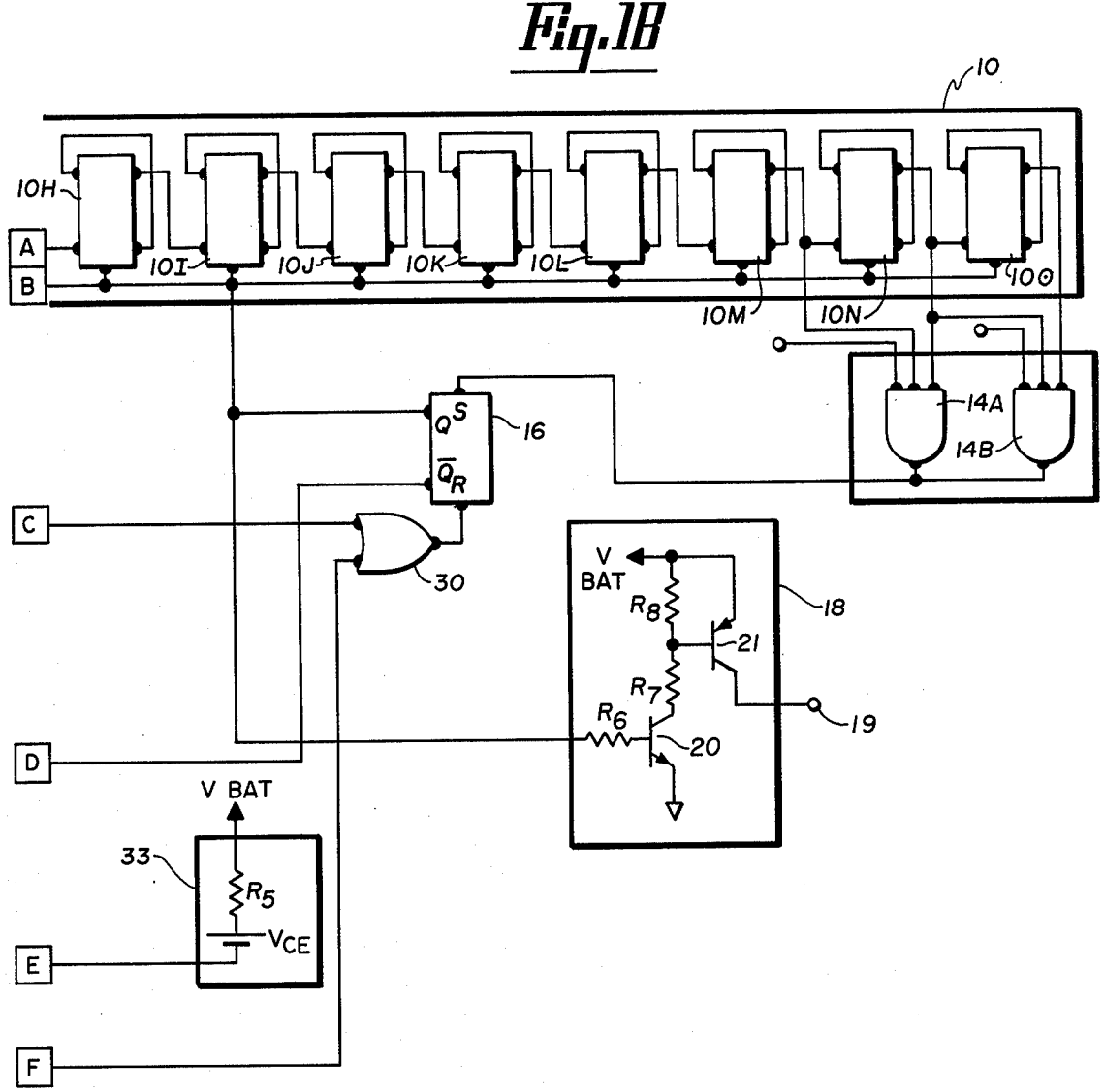

Referring now to FIGS. 1A and 1B, a pulse generating circuit for use in a pacemaker is shown. The system can be operated alone, as shown, to provide an open loop constant pulse energy pacing circuit. However, nothing herein should be construed as limiting the invention described herein to use in an open loop pacemaker system. The subject invention can also be readily incorporated into a programmable pacemaker system of the sort shown in the above-identified patent application to McDonald, entitled "Digital Cardiac Pacemaker".

The XTAL signal shown in FIG. 1 is a generally square wave pulse signal occurring at a frequency of 32,768 Hertz. The XTAL signal is connected to the clock inputs of a rate counter 10 and an interval counter 12.

Rate counter 10 is, in the preferred embodiment shown, a 15 stage binary counter, connected in a known manner. The outputs from stages 10 M, 10 N and 10 O, are shown connected to the inputs of the next stage of rate counter 10 and to AND gates 14A and 14B, which, when their inputs receive all ones, drive the set input of an RS flip-flop 16. Flip-flop 16 in turn drives an output circuit 18. When the set input switches to a high level, the Q output of flip-flop 16 switches to a high output and resets the rate counter flip-flops 10 and returns the set input to a low level. At the same time, the Q output of flip-flop 16 drives an output pulse from output circuit 18, which is in turn applied to the heart by known means.

The $\bar{Q}$ output of flip-flop 16 is connected to the reset input of the counters of interval counter 12, which, in the preferred embodiment shown, is a six stage binary counter connected in a conventional manner. When the set input is applied to flip-flop 16, the $\bar{Q}$ output switches from a high to a low signal to remove the reset command from the reset inputs of interval counter 12.

Figure 2:
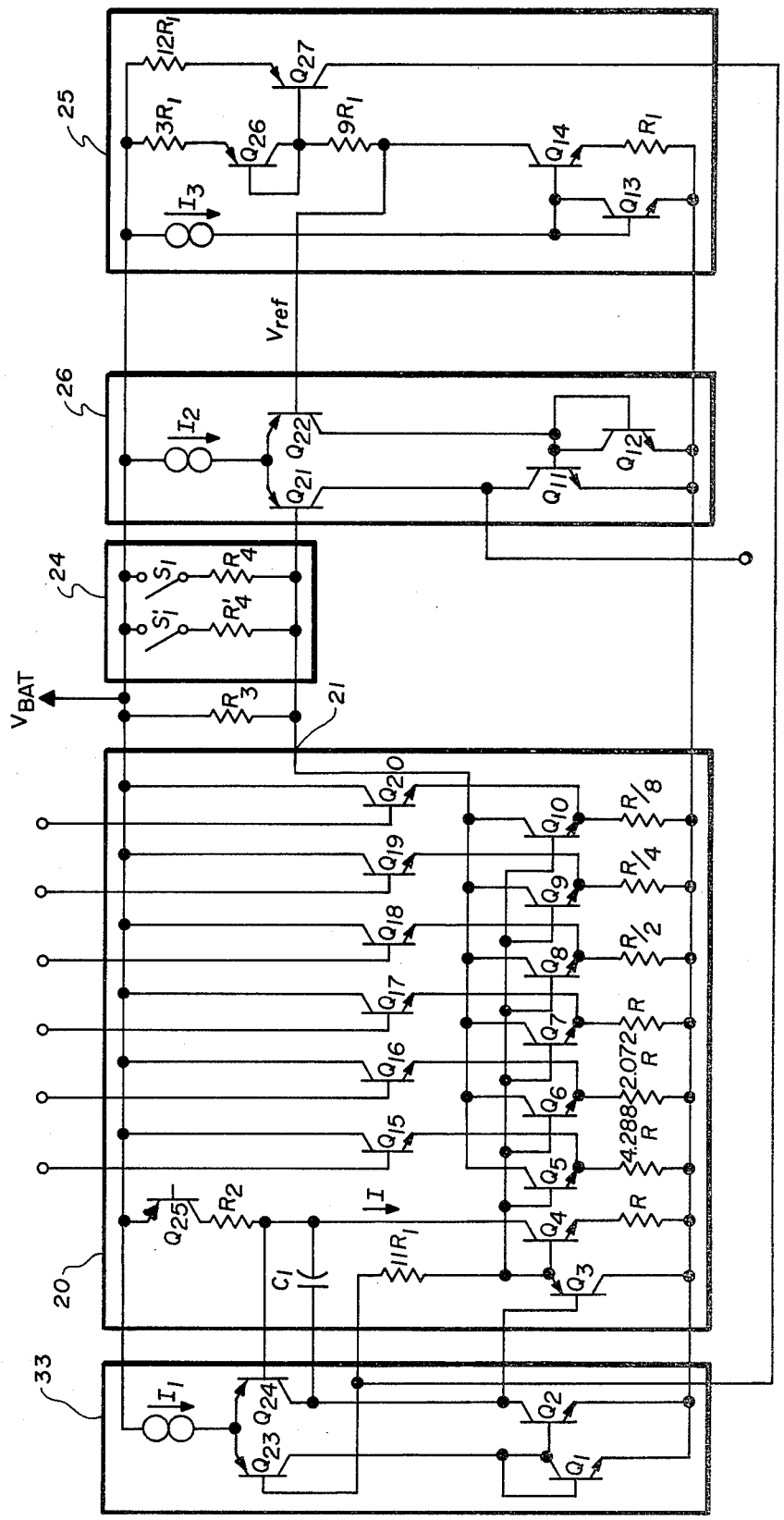
FIG. 2 shows the detailed schematic of a digital to analog converter which is particularly useful in the pacing circuit shown in FIGS. 1A and 1B.

When the interval counter 12 resets are held low, they start to count the XTAL signal at zero count. The outputs of each stage of the interval counter 12 are connected to a digital to analog converter 20, the detailed circuitry for which is shown in FIG. 2. The analog converter produces zero output current at terminal 21 for a zero input from interval counter 12 corresponding to zeroes at the outputs of stages 12A through 12F. The output current from terminal 21 of D to A converter 20 is applied to a resistor 24.

Resistor 24 is shown as a series of parallel resistors $R_4$, $R_4'$, and $R_4''$, which may be connected in varying combinations using switches $S_1$, $S_1'$, and $S_1''$ to vary the resistance of resistor 24 to permit adjustment of the pulse energy which is to then be held constant.

When the potential across resistor 24 reaches the voltage $V_{ref}$ on the other input of comparator 26, the output at terminal 27 of comparator 26 goes high and applies, through OR gate 30, a reset signal to flip-flop 16. This reset signal resets output flip-flop 16, removing the drive signal to output circuit 18 to terminate the pacing pulse, and removing the reset signal from the reset inputs of rate counter 10 to enable that counter to resume counting of the XTAL signal. The resetting of flip-flop 16 also resets the interval or width counter 12.

To achieve the desired pulse width sensitivity to supply voltage variation to achieve constant pulse energy, resistor R5 is used in connection with $V_{CE}$ to drive the digital to analog converter input 32. The amount of current driven into the input port 32 of the digital to analog converter 20 determines the amount of current delivered at the output 21 of converter 20 for each bit of input. As the supply voltage, $V_{BAT}$, decreases, the input current to converter 20 also decreases, thereby increasing the pulse width because a higher count in counter 12 is needed to increase the output current at terminal 21 to produce the condition where the $V_{ref}$ appears across resistor 24. Different nominal pulse widths can be obtained by selectively closing a desired number of switches $S_1$, $S_1'$, and $S_1''$ to vary the resistance of resistor 24 between the output terminal 21 of the digital to analog converter, and the positive supply voltage $V_{BAT}$.

The circuit of FIG. 1 also includes a safety feature which is operative in the event of a decrease of supply voltage below the point where the output current at terminal 21 of the digital to analog converter 20 is sufficient to produce a voltage equal to $V_{ref}$ across resistor 24. The safety feature is provided by AND gate 34, which senses the point at which all flip-flops in counter 12 switch to high levels to reset the output flip-flop 16 through OR gate 30 to terminate the pacing pulse after a predetermined pulse duration.

The advantage provided by the above-described system is significant. Elimination of the necessity of using a voltage controlled oscillator eliminates the inherent problems of drift and trimming of the VCO. Elimination of the VCO also makes it much more feasible to integrate the circuitry of such on a single chip, while minimizing the necessity for external components such as a VCO capacitor.

The pacing circuit of FIGS. 1A and 1B also has an advantage over prior art circuits, since it eliminates the need for "fast" counter loops as described in the McDonald patent application Ser. No. 957,958, discussed above. Use of the present invention as shown in FIG. 1 permits integration of the circuitry to produce a circuit with a lower overall current drain.

FIG. 2 shows a possible integrated circuit configuration to implement the analog to digital converter 20, the comparator 26, the reference voltage source 25, the source of current 33 for D to A converter 20, and the resistor 24, which are used to provide the initial selection of the pulse width whose energy is to be held constant by variation of its width in accordance with variation in the supply voltage.

The basic digital to analog function of block 20 is performed by transistors Q4 through Q10 in conjunction with emitter resistors having resistances R, 4.288R, 2.072R, R, R/2, R/4, and R/8. The digital to analog bit current is established by the collector current of Q4, and is weighted for larger bits by area scaling devices. The base leads of Q15 through Q20 are connected to the respective outputs of the six stages of the width counter 12. The transistors Q15 through Q20 are individually turned on when their respective flip-flops in counter 12 turn them on to turn off their bits by back biasing of the appropriate transistors of Q5 through Q10 to reduce the current at terminal 21 of the digital to analog converter.

The bias for the digital to analog portion of the circuit is supplied by the current generator $I_3$ in block 25. Q13 and Q14 and Q26 in that block are used to generate a positive temperature compensated voltage across the emitter resistor of Q14. Q14 has an emitter area five times larger than Q13, which causes the voltage across $R_1$, $V_{ref}$, to be approximately 42 millivolts if $R_1$ is chosen so that its current is equal to $I_3$. The current through Q14 is therefore "multiplied up" by $9R_1$ and $3R_1$ in series with Q26 to approximately +2 mv/°C. This value equals the negative 2 mv/°C. of Q26 connected as a diode and provides a voltage $V_{ref}$ of 1.25 volts which is the reference voltage of block 25, which is connected to the base of Q22 of comparator 26.

Q26 of the reference block 25 is used to generate a temperature compensated reference current and, through Q27, to drive the resistor designated $11R_1$ to the base of transistor Q4. The voltage across resistor $11R_1$ will have an approximately +2 mv/°C. voltage across, which in conjunction with the $V_{be}$ of Q4, gives a $V_{ce}$ of 1.20 volts.

Block 33 includes a current source $I_1$ which provides a bias current for Q23, Q24, Q1, Q2, and Q3, which form the drive circuitry for the bases of the digital to analog transistors Q5 through Q10 and their scaling resistors. Capacitor $C_1$ is used to stabilize the loop.

Transistor Q25 in the digital to analog converter 20 is used as a switch to turn resistor R2 on only during the output pulse generating portion of the circuit of FIG. 1. The current through R2, designated "I" will be in the input current for the digital to analog converter circuit. The current I has the following value:

$$I=(V_{bat}-V_{ce})/(R_2+R)$$

The voltage out of the digital to analog converter is:

$$V_{D\,to\,A}=(I)(R_3)(N)/4=(R_3)(V_{bat}-V_{ce})N/(R_2+R)(4)$$

The equation for the voltage is divided by four to reflect the choice of scaling resistors and resistor values which were selected to make I equal to four times the minimum bit current. In the above equation, N is the number of clock cycles.

Rearranging the above equations slightly, the number of clock cycles which determine the length of the pulse are given by the expression:

$$"N=(R_2+R)(V_{d2a})(4)/R_3(V_{bat}-V_{ce})"$$

and the time duration of the pulse with $T_{pw}$ is:

$$"T_{pw}=(N/32.768\,KHZ=R_2+R)(V_{d2a})(4)/R_3(V_{bat}-V_{ce})(32.768\,KHZ)"$$

A circuit for comparator 26 is shown in FIG. 2 formed by $I_2$, Q21, Q22, Q11, and Q12. The voltage $V_{ref}$ is connected to the base of Q22 and compared to the voltage out of the digital to analog converter at the base of Q21 and the comparator output is produced at the common collectors of Q11 and Q21.

Variation of $R_3$ can be accomplished by selectively closing various switches in box 24 to vary resistor $R_3$ to select different basic pulse widths which can then be regulated without other modifications to the circuit.

Having described the invention, the embodiments thereof in which an exclusive property right is claimed are defined in the following claims.

I claim:

1. In an electromedical pulse generator used to stimulate a selected portion of an animal body, said generator of the type having terminal means adapted for connection to an electrical lead and having power source means and electrical pulse generating means electrically connected to the power source means for supplying output pulses at a predetermined rate to the terminal means, each pulse having a predetermined nominal pulse width and a predetermined pulse energy, the improvement comprising:
   (a) timing means for providing a digital output signal having a value proportional to the elapsed time following generation of the leading edge of an output pulse;
   (b) digital to analog converter means connected to said timing means for receiving said digital output signal therefrom and to said power source means to provide an analog output signal representative of said digital output signal which increases with time at a rate inversely proportional to the voltage of said power source; and
   (c) comparator means connected to receive the analog output signal from said digital to analog converter means, said comparator means constructed and arranged for providing a signal to terminate said output pulse when said analog output signal reaches a predetermined level.

2. In a digital cardiac pacemaker pulse generator for providing cardiac stimulating pulses said pulse generator including clock means for providing a series of clock pulses at a fixed frequency; counter means responsive to said clock means for counting said clock pulses; decoding means responsive to the count of said counter means for providing signals upon said counter means reaching a certain count manifesting the leading edge of said cardiac stimulating pulses; battery means for providing a decreasing magnitude voltage over an extended period of time; and output means for providing said cardiac stimulating pulses in response to said decoding means, said cardiac stimulating pulses having a voltage amplitude related to and decreasing with said battery voltage; the improvement comprising:
   (a) converter means for providing an output voltage which increases in predetermined increments which have a magnitude proportional to the magnitude of said battery voltage for each count after the count manifesting the leading edge of said leading edge of said stimulating pulse is reached; and
   (b) comparator means connected to receive the output voltage from said converter means and connected to said output means, said comparator means constructed and arranged for terminating said stimulating pulse when the output voltage of said converter means reaches a predetermined level.

3. The invention according to claim 2 wherein the relationship of the predetermined increments of the output voltage of said converter means to said battery voltage increases the time between the leading edges of said cardiac stimulating pulses and the termination of said pulse as said battery voltage decreases to minimize the diminution of pulse energy of said cardiac stimulating pulses.

4. A digital cardiac pacemaker pulse generator for providing a cardiac stimulating pulse comprising:
   (a) battery means for providing a voltage level which changes with time;
   (b) clock means for providing a chain of clock pulses having a fixed frequency;
   (c) timing means for providing a rate signal for initiation of said cardiac stimulating pulse at a predetermined repetition rate;
   (d) interval counter means connected to said clock means to receive clock pulses therefrom and for counting said clock pulses, said interval counter means constructed and arranged for receiving said rate signal from said timing means and for resetting said counter means in response to said rate signal;
   (e) digital to analog converter means connected to said battery means and said interval counter means, said converter means constructed and arranged for providing an analog output voltage which increases in predetermined increments in accordance with the content of said interval counter means and wherein the magnitude of each of said increments is proportioned to the voltage level of said battery means; and
   (f) output means connected to said battery means and to said timing means to receive said rate signal therefrom, said output means constructed and arranged for turning on said cardiac stimulating pulse in response to said rate signal, said output means also constructed and arranged for providing and stimulating pulses at an amplitude proportional to the voltage level of said battery means, said output means also connected to said digital to analog converter means to receive the analog output voltage therefrom and constructed and arranged for turning off said cardiac stimulating pulse when the analog output voltage of said digital to analog converter means exceeds a predetermined reference value, said reference value having a value selected to increase the pulse width of said cardiac stimulating pulses as the voltage level of said battery means decreases with time.

5. The invention of claim 4 wherein protective means are provided for supplying a cutoff signal to said output means for terminating said cardiac stimulating pulse if a predetermined count has been reached on said interval counter means if said cardiac stimulating pulse has not already been terminated by the analog output voltage generated by said digital to analog comparator means.

6. The invention of claim 4 wherein said digital to analog converter means has digital inputs connected to successive stages of said interval counter means and an analog input connected to said battery means to receive a voltage having a magnitude which changes proportional to the change of the voltage level of said battery means.

* * * * *

UNITED STATES PATENT AND TRADEMARK OFFICE
CERTIFICATE OF CORRECTION

PATENT NO. : 4,278,094
DATED : July 14, 1981
INVENTOR(S) : Don W. Zobel

It is certified that error appears in the above—identified patent and that said Letters Patent is hereby corrected as shown below:

Column 6, line 65, "and", second occurrence, should read

-- said --.

Signed and Sealed this

*Twenty-second* Day of *September 1981*

[SEAL]

*Attest:*

*Attesting Officer*

GERALD J. MOSSINGHOFF
*Commissioner of Patents and Trademarks*